(12) United States Patent
Gorman, III et al.

(10) Patent No.: US 8,473,036 B2
(45) Date of Patent: Jun. 25, 2013

(54) IN VIVO MEASUREMENT OF MITOCHONDRIAL FUNCTION

(75) Inventors: Joseph H. Gorman, III, Lower Gwynedd, PA (US); Robert C. Gorman, Lower Gwynedd, PA (US); Mahsa Ranji, Milwaukee, WI (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 100 days.

(21) Appl. No.: 12/935,755

(22) PCT Filed: Apr. 1, 2009

(86) PCT No.: PCT/US2009/039098
§ 371 (c)(1),
(2), (4) Date: Mar. 22, 2011

(87) PCT Pub. No.: WO2009/124114
PCT Pub. Date: Oct. 8, 2009

(65) Prior Publication Data
US 2011/0288418 A1    Nov. 24, 2011

Related U.S. Application Data

(60) Provisional application No. 61/041,643, filed on Apr. 2, 2008.

(51) Int. Cl.
*A61B 6/00* (2006.01)
(52) U.S. Cl.
USPC .......................................... 600/476; 600/477
(58) Field of Classification Search
USPC ................................................. 600/473–480
See application file for complete search history.

(56) References Cited

U.S. PATENT DOCUMENTS

| | | | |
|---|---|---|---|
| 3,811,777 A * | 5/1974 | Chance | 356/73 |
| 5,685,306 A | 11/1997 | Davidson | |
| 5,792,051 A * | 8/1998 | Chance | 600/310 |
| 5,916,171 A * | 6/1999 | Mayevsky | 600/476 |

(Continued)

FOREIGN PATENT DOCUMENTS

WO    WO 2009/124114    10/2009

OTHER PUBLICATIONS

Argaud et al., "Specific inhibition of the mitochondrial permeability transition prevents lethal reperfusion injury", J. Mol. Cell Cardiol., Feb. 2005, 38(2), 367-374.

(Continued)

*Primary Examiner* — Sanjay Cattungal
(74) *Attorney, Agent, or Firm* — Woodcock Washburn, LLP

(57) ABSTRACT

Disclosed herein are devices for assessing mitochondrial function in a living subject comprising a catheter comprising a sheath defining a lumen, a distal end, and a proximal end comprising a light guide for radiating light onto a target within the subject and for receiving a fluorescence signal from the target; a light source, wherein the catheter is adapted for transmitting light from the light source to the light guide; and, a detector for receiving the fluorescence signal from the light guide and for correlating the fluorescence signal to the mitochondrial function of the target. Also disclosed are methods for assessing mitochondrial function in a living subject comprising placing a catheter proximate to a site of interest within the subject; using the catheter to acquire fluorescence signals from cells at the site of interest; and, correlating the fluorescence signals to the mitochondrial function of the cells.

15 Claims, 4 Drawing Sheets

U.S. PATENT DOCUMENTS

| | | | | |
|---|---|---|---|---|
| 6,826,422 | B1* | 11/2004 | Modell et al. | 600/407 |
| 7,130,672 | B2* | 10/2006 | Pewzner et al. | 600/324 |
| 7,313,424 | B2* | 12/2007 | Mayevsky et al. | 600/310 |
| 7,364,551 | B2* | 4/2008 | Allen et al. | 600/532 |
| 7,587,236 | B2* | 9/2009 | Demos et al. | 600/477 |
| 8,064,976 | B2* | 11/2011 | Ince | 600/343 |
| 2005/0234315 | A1* | 10/2005 | Mayevsky et al. | 600/310 |
| 2006/0052709 | A1* | 3/2006 | DeBaryshe et al. | 600/476 |
| 2006/0184037 | A1* | 8/2006 | Ince et al. | 600/476 |
| 2006/0195022 | A1* | 8/2006 | Trepagnier et al. | 600/316 |
| 2006/0241364 | A1* | 10/2006 | Ince | 600/323 |
| 2007/0179366 | A1* | 8/2007 | Pewzner et al. | 600/310 |
| 2007/0179571 | A1 | 8/2007 | De Taboada et al. | |
| 2007/0232874 | A1* | 10/2007 | Ince | 600/320 |
| 2009/0012378 | A1* | 1/2009 | Ince | 600/322 |
| 2009/0093807 | A1* | 4/2009 | Hyde et al. | 606/34 |
| 2010/0312081 | A1* | 12/2010 | Benaron et al. | 600/323 |
| 2011/0288418 | A1* | 11/2011 | Gorman et al. | 600/479 |
| 2012/0053429 | A1* | 3/2012 | Trepagnier et al. | 600/310 |
| 2012/0089031 | A1* | 4/2012 | Ince | 600/476 |
| 2012/0190964 | A1* | 7/2012 | Hyde et al. | 600/407 |

OTHER PUBLICATIONS

Bromme et al., "Apoptosis in the heart: when and why?", Mol Cell Biochem, Oct.-Nov. 1996, 163-164, 261-275.

Chance et al., "High and low energy states of cytochromes. II. In submitochondrial particles", J Biol Chem, Oct. 1966, 241(20), 4577-4587.

Chance et al., "Respiratory enzymes in oxidative phosphorylation. VII. Binding of intramitochondrial reduced pyridine Nucleotide", J. Biol Chem, Sep. 1958, 233(3), 736-739.

Duchen et al., "On the involvement of a cyclosporin A sensitive mitochondrial pore in myocardial reperfusion injury", Cardiovasc Res, Oct. 1993, 27(10), 1790-1794.

Gottlieb et al., "Reperfusion injury induces apoptosis in rabbit cardiomyocytes", J Clin Invest, Oct. 1994, 94(4), 1621-1628.

Hartung et al., "Targeting of Matrix Metalloproteinase Activation for Noninvasive Detection of Vulnerable Atherosclerotic Lesions", Eur J Nucl Med Mol Imaging, Jun. 2007, 34(Suppl 1), S1-8.

Isobe et al., "Noninvasive Imaging of Atherosclerotic Lesions in Apolipoprotein E-deficient and Low-density-lipoprotein Receptor-Deficient Mice With Annexin A5", J. Nucl Med., Sep. 2006, 47(9), 1497-1505.

Kietselaer et al., "Noninvasive Detection of Programmed Cell Loss With $^{99m}$Tc-Labeled Annexin in A5 in Heart Failure", J. Nucl Med., Apr. 2007, 48(4), 562-567.

Kroemer et al., "The mitochondrial death/life regulator in apoptosis and necrosis", Annu Rev Physiol, Oct. 1998, 60, 619-642.

Leshnower et al., "Role of acetaminophen in acute myocardial infarction", Am J Physiol Heart Circ Physiol, Jun. 2006, 290(6), H2424-H2431.

Mayevsky et al., "Mitochondrial Dysfunction: Bench-to-Bedside Optical Monitoring of Tissue Vitality", J Biomed Optical Spectroscopy, Feb. 2008, 6853, 1605-7422.

Mayfield et al., "*Chlamydomonas reinhardtii* Chloroplasts as Protein Factories", Curr Op in Biotech., Apr. 2007, 18(2), 126-133.

Narula et al., "Annexin-V imaging for noninvasive detection of cardiac allograft rejection", Nat Med, Dec. 2001, 7(12), 1347-1352.

Narula et al., "Apoptosis in myocytes in end-stage heart failure", N. Engl J. Med, Oct. 1996, 335(16), 1182-1189.

Ranji et al., "Fluorescence spectroscopy and imaging of myocardial apoptosis", J Biomed Opt, Nov.-Dec. 2006, 11(6), 064036.

Ranji et al., "Quantifying acute myocardial injury using ratiometric fluorometry", submitted to IEEE Transaction on Biomedical Engineering (TBME), May 2009, 56(5), 1556-1563.

Zoratti et al., "The mitochondrial permeability transition", Bichim Biophys Acta, Jul. 1995, 1241(2), 139-176.

Anderson and Meyer, "In vivo fluorescent imaging of NADH redox state in brain," Methods Enzymol., 2002, 352, 482-494.

Bassett et al., "Respiratory activity of lung mitochondria isolated from oxygen-exposed rats," Am. J. Physiol., Oct. 1992, 263(4 Part 1), L439-L445.

Chance et al., "Oxidation-reduction ratio studies of mitochondria in freeze-trapped samples. NADH and flavoprotein fluorescence signals," J. Biol. Chem., Jun. 10, 1979, 254(11), 4764-4771.

Fisher et al., "Evaluation of redox state of isolated perfused rat lung," Am. J. Physiol., May 1976, 230(5), 1198-1204.

Matsubara et al., "In Vivo Fluorometric Assessment of Cyclosporine on Mitochondrial Function During Myocardial Ischemia and Reperfusion," Annals of Thoracic Surgery, May 2010, 89(5), 1532-1537.

Mayevsky and Barbiro-Michaely, "Use of NADH fluorescence to determine mitochondrial function in vivo," International Journal of Biochemistry & Cell Biology, Oct. 2009, 41(10), 1977-1988.

* cited by examiner

US 8,473,036 B2

IN VIVO MEASUREMENT OF MITOCHONDRIAL FUNCTION

CROSS-REFERENCE TO RELATED APPLICATIONS

This application is the National Stage of International Application No. PCT/US2009/039098, filed Apr. 1, 2009, which claims the benefit of U.S. Provisional Application No. 61/041,643, filed Apr. 2, 2008, the disclosures of which are incorporated herein by reference in their entireties.

GOVERNMENT RIGHTS

Research leading to the disclosed invention was funded, in part, by the National U.S. National Institutes of Health (Bethesda, Md.) HL63954 (Robert C. Gorman), HL76560 (Joseph H. Gorman), HL71137 (Robert C. Gorman) and IME grant. Accordingly, the United States Government may have rights in the invention described herein.

FIELD OF THE INVENTION

The present invention pertains to the assessment of mitochondrial function and the potential for cell death in a tissue or other areas in which cells are found.

BACKGROUND OF THE INVENTION

Over the past 35 years techniques to identify and revascularize ischemic myocardium have been developed to a high level. However, despite such efforts, a mass epidemic of congestive heart failure (CHF) due to coronary disease has developed. Five million Americans suffer from CHF with 550,000 new cases diagnosed each year. Sixty-eight percent of these cases are due to coronary disease. After myocardial infarction (MI) CHF is preceded by infarct expansion, progressive generalized left ventricular (LV) dilatation and contractile dysfunction. This deleteriously progressive phenomenon has been termed post-infarction LV remodeling.

Once the remodeling process is established and symptoms of CHF ensue, five year survival, even with the most aggressive medical and surgical therapy is about 50%. These dismal results have generated a strong interest in developing mechanical strategies for preventing infarct expansion, the resulting LV dilation and failure.

Recent work in chronic large animal heart failure models has demonstrated early restraint to prevent infarct stretching significantly limits ventricular dilation and preserves function. Despite compelling experimental data these techniques currently have limited clinical applicability due to an inability to identify patients early (days after infarction) at risk for remodeling. While infarct size has long been understood to correlate with the ultimate degree of ventricular remodeling, it is a difficult parameter to quantify particularly early after reperfusion therapy.

Apoptosis, or programmed cell death, is known to play a role in the decline of ventricular function in heart failure, for example, in myocardial infarction and heart transplant rejection. In addition, apoptosis is implicated in the disruption of atherosclerotic plaques, which account for more than two-thirds of acute coronary events; plaques that are vulnerable to rupture can demonstrate large necrotic cores and positive remodeling of the sclerotic vessel. Apoptosis comprises a series of genetically programmed events, and is potentially reversible or can otherwise be responsive to intervention, and therefore techniques for detecting apoptotic potential can be used to identify suitable targets for antiapoptotic intervention. Using animal models, antiapoptotic intervention has been shown to delay, prevent the occurrence of, or minimize the severity of heart failure.

Numerous molecular methods for identifying vulnerable atherosclerotic lesions or programmed cell death in myocardial infarction and heart transplant tissue. Wu J C, Narula J, *Curr Op in Biotech.* 2007, 18:1-3. For example, recent studies have used measurements of matrix metalloproteinase (MMP) expression to identify atherosclerotic plaques that are prone to rupture. See Hartung D, et al., *Eur J Nucl Med Mol Imaging.* 2007 June; 34 Suppl 1:S1-8. Radiolabeled Annexin A5, a protein that has been proposed to predict the likelihood of acute vascular events, has been used for the noninvasive imaging of atherosclerosis in transgenic mouse models (Isobe S, et al., *J Nucl Med.* 2006 September; 47(9):1497-505), and for the noninvasive detection of programmed cell death in heart failure patients (Kietselaer B L, *J Nucl Med.* 2007 April; 48(4): 562-7). However, molecular methods have proven to be of limited efficacy and, importantly, do not enable early-stage detection of coronary events. Early detection of possible plaque rupture and early assessment of myocardial injury would permit timely intervention and preserve a wider range of therapeutic options with respect to a given patient.

Given the extremely widespread prevalence of coronary disease and the uncertainty surrounding both the extent of myocardial injury following an ischemic event and the stability of ostensibly non-threatening vascular occlusions, methods and devices for the accurate in vivo assessment of mitochondrial function would be of considerable clinical value.

SUMMARY

Disclosed herein are devices for assessing mitochondrial function in a living subject comprising a catheter comprising a sheath defining a lumen, a distal end, and a proximal end comprising a light guide for radiating light onto a target within the subject and for receiving a fluorescence signal from the target; a light source, wherein the catheter is adapted for transmitting light from the light source to the light guide; and, a detector for receiving the fluorescence signal from the light guide and for correlating the fluorescence signal to the mitochondrial function of the target.

Also disclosed are methods for assessing mitochondrial function in a living subject comprising placing a catheter proximate to a site of interest within the subject; using the catheter to acquire fluorescence signals from cells at the site of interest; and, correlating the fluorescence signals to the mitochondrial function of the cells.

DETAILED DESCRIPTION

Figure 1:
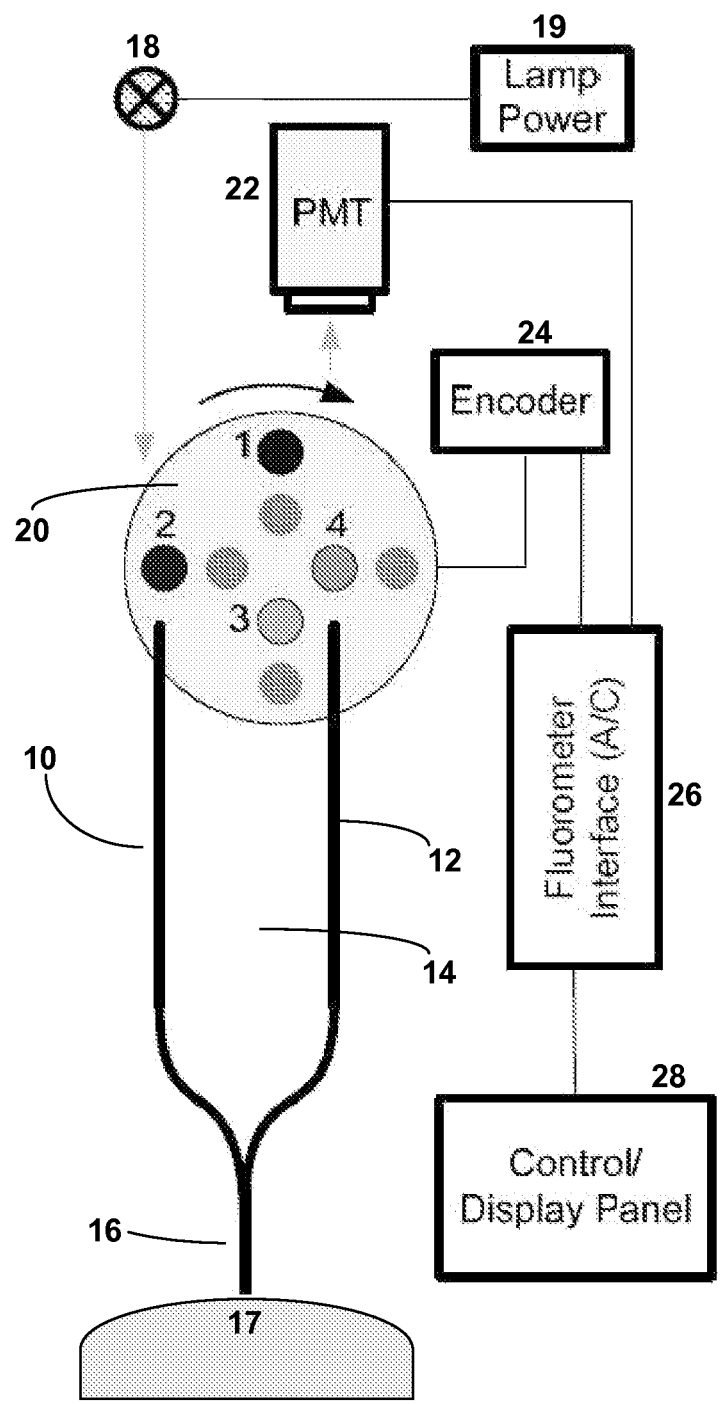
FIG. 1 provides a schematic drawing of an embodiment of the inventive mobile optical-electrical fluorometry apparatus.

The present invention may be understood more readily by reference to the following detailed description taken in connection with the accompanying figures and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

In the present disclosure the singular forms "a," "an," and "the" include the plural reference, and reference to a particular numerical value includes at least that particular value, unless the context clearly indicates otherwise. Thus, for example, a reference to "a lumen" is a reference to one or more of such lumens and equivalents thereof known to those skilled in the art, and so forth. When values are expressed as approximations, by use of the antecedent "about," it will be understood that the particular value forms another embodiment. As used herein, "about X" (where X is a numerical value) refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable.

The disclosures of each patent, patent application, and publication cited or described in this document are hereby incorporated herein by reference, in their entirety.

Mitochondrial dysfunction and disruption are known to be intimately involved in both necrotic and apoptotic processes that lead to cell death following myocardial reperfusion. Gottlieb R A, et al., Reperfusion injury induces apoptosis in rabbit cardiomyocytes, *J Clin Invest, vol.* 94, no. 4, pp 1621-1628, October 1994; Bromme H J & Holtz J. *Apoptosis in the heart: when and why? Mol Cell Biochem*, pp 163-164: 261-275, October-November 1996. Inflammation and apoptosis play important roles in the vulnerability of apoptotic plaques to rupture and initiation of acute coronary events. Hartung D, et al., *Eur J Nucl Med Mol Imaging.* 2007 June; 34 Suppl 1:S1-8. Presently, the assessment of infarct size is generally limited to angiographic and echocardiographic techniques, and molecular methods of assessing the extent of myocardial injury or the risk of plaque rupture are subject to numerous limitations.

The present invention is directed to in vivo quantitative assessment of mitochondrial function that can be used to evaluate, for example, necrotic potential, the apoptotic potential, the risk of atherosclerotic rupture, metabolic factors, and other characteristics of the cells at or near a target area or site of interest. The evaluation of such characteristics can provide extremely pertinent, sometimes critical information. For example, the present invention permits an assessment infarct size with greater efficacy than what is currently provided by angiography and echocardiography. Likewise, evaluation of mitochondrial function and potential for programmed cell death in a living subject can be used to predict the vulnerability of an otherwise hemodymanically insignificant atherosclerotic plaque to rupture, and therefore to predict the likelihood of an acute cardiac event. Furthermore, information that may be acquired pursuant to the present invention may be done so with reliable efficacy at a much earlier stage in time than existing methodologies. For example, the assessment of mitochondrial function may be used to determine the degree of myocardial injury and the area at risk for tissue mortality as early as 15 minutes after reperfusion of infarcted tissue, which represents an extremely early window into the process of cell death in ischemic cardiac tissue.

To this end and others, the present invention is directed to an optical catheter-based device that can be used to acquire fluorescence signals of the intrinsic mitochondrial fluorophores, nicotinamide adenine dinucleotide (NADH) and flavoprotein (FP). The ratio of these fluorescence signals (FP/FP+NADH), defined as the redox ratio (RR), has been shown to correlate with different metabolic states and mitochondrial function. Chance B & Baltscheffsky H., *Respiratory enzymes in oxidative phosphorylation. VII. Binding of intramitochondrial reduced pyridine Nucleotide, J Biol Chem*, vol. 233, no. 3, pp 736-739, September 1958; Chance B, and Schoener B. *High and low energy states of cytochromes. II. In submitochondrial particles, J Biol Chem*, vol. 241, no. 20, pp 4577-4587, October 1966. Additionally, the RR has been shown to undergo an oxidative shift in tumor cells with mitochondrial dysfunction associated with apoptosis. Ranji M, et al., *Fluorescence spectroscopy and imaging of myocardial apoptosis, J Biomed Opt*, vol. 11, no. 6, pp 064036, November-December 2006. It has presently been discovered that the redox ratio within the ischemic zone, as measured by the inventive devices, can be directly correlated with, inter alia, infarct size early after myocardial reperfusion. As disclosed herein, evaluation of mitochondrial fluorescence can be a quantitative tool to assess myocardial injury without invasive tissue biopsy.

Disclosed herein are devices for assessing mitochondrial function in a living subject comprising a catheter comprising a sheath defining a lumen, a distal end, and a proximal end comprising a light guide for radiating light onto a target within the subject and for receiving a fluorescence signal from the target; a light source, wherein the catheter is adapted for transmitting light from the light source to the light guide; and, a detector for receiving the fluorescence signal from the light guide and for correlating the fluorescence signal to the mitochondrial function of the target.

Also disclosed are methods for assessing mitochondrial function in a living subject comprising placing a catheter proximate to a site of interest within the subject; using the catheter to acquire fluorescence signals from cells at the site of interest; and, correlating the fluorescence signals to the mitochondrial function of the cells. In preferred embodiments, the catheter for use in the inventive methods comprising a sheath defining a lumen, a distal end, and a proximal end comprising a light guide for radiating light onto a target within the subject and for receiving a fluorescence signal from the target; and, a light source, wherein the catheter is adapted for transmitting light from the light source to the light guide.

The instant catheters may have a length of about 20 cm to about 200 cm from the distal end (defined herein as the end closest to the operator of the device while in use) to the proximal end. The outer diameter of the catheter may be about 1 mm to about 10 mm, depending on the desired end use. For example, when used to assess the stability of an atherosclerotic obstruction of arterial blood vessel, the catheter may have an outer diameter of about 3 mm or less.

The catheters may be adapted for insertion into a patient through the working channel of a second catheter. Additionally or alternatively, the catheter may further comprise at least one lumen that is compatible for use with a guidewire, i.e., for translation of the catheter along a guidewire. The instant devices may also be adapted for percutaneous insertion into the subject. The characteristics of such catheters, such as the arrangement and dimensions of their constituent components, are widely known among those skilled in the art.

Preferable materials for the catheter include those that are compatible with medical treatment of human subjects, and to this end, biocompatible surgical materials are highly preferred. For example, polyimide, polyethylene, polypropylene, Kalrez®, Simriz®, Viton®, Chemraz®, silicone, neoprene, nitrile, metal or metal alloys (such as Ti—Nb—Zr; see, e.g., U.S. Pat. No. 5,685,306) or any other combination thereof may be used. The materials used for the construction of the catheter, as well as the methods for the construction thereof, are readily appreciated by those skilled in the art, and all appropriate materials and means of construction are contemplated herein.

Optimally, the devices are capable of being manually or mechanically operated. Therefore, the device may further comprise a hand-piece operatively connected to the catheter. The light activation, filtration, and fluorescence detection and processing functionalities of the instant device are preferably controlled via a controlling unit that is operatively connected to the catheter. Preferred controlling units may be operated by a human or automatically according to preset specifications.

The light source is present in the instant device in order to provide illumination of a target within a subject via the catheter. Accordingly, the instant catheter is adapted for transmitting light from the light source to the target. The catheter may be fitted with a material that permits translation of light from the light source to the proximal end of the catheter, such as optical waveguide material, and in particular, optical fiber material. The optical fiber material preferably comprises a bundle of semi-rigid optical fibers, such that the instant catheter is imparted with flexibility and manipulability during deployment and while in situ. Suitable optical fibers are single-mode or multi-mode fibers, various examples of which are readily identified among those skilled in the art.

The light source can comprise any light emitting appliance. Preferably, the light source comprises a broadband lamp that is capable of full-spectrum radiance, such as an arc lamp. Exemplary arc lamps include carbon, neon, argon, xenon, krypton, sodium, metal halide, and mercury arc lamps. Advantageously, broadband lamps are relatively inexpensive and safe, and many varieties are already approved by the Food and Drug Administration for irradiation of human tissue. Alternatively, the light source can comprise a laser, a diode, or any other appliance that is capable of providing light energy for translation along some length of the catheter (whether the entire length of the catheter or a portion thereof). The light source may be housed within the lumen of the catheter, or may be external to the catheter but positioned so that light that is emitted therefrom is transmitted to the catheter. In a preferred embodiment, the light source comprises an arc lamp that is located at or near the distal end of the catheter and positioned such that a substantial portion of the light emitted from the lamp is transmitted to the lumen via the distal end of the catheter. Where the catheter is fitted with a fiber optic material, the light entering the distal end of the catheter is translated along the length of the catheter to the proximal end, the fidelity of such light translation being dependent upon the characteristics of the fiber optic material. In an alternative embodiment, the light source may be one or more diodes that is/are housed within the lumen of the catheter at some point along its length. Due to the size limitations of the catheter, the width of any such diode should be the same size or smaller than the inner diameter of the lumen. The light that is emitted from the diode(s) is translated across the length of the catheter that is between the diode and the proximal end of the catheter, via the lumen. A diode may be broadband or may be capable of emitting light at a desired wavelength or wavelengths. In yet another embodiment, the light source emits a laser at one or more wavelengths, or the light source comprises multiple devices that each emits a laser at a desired wavelength. Conventional lasers or laser diodes are examples. Although preferably any laser-based light source is positioned at or near the distal end of the catheter such that a substantial portion of the light emitted from the lamp is transmitted to the distal end if the catheter, a laser-based light source may be housed within the lumen of the catheter under the conditions described previously with respect to the diode light source.

The light source may be adapted for emitting light at a desired wavelength (e.g., a laser or single-wavelength diode or laser diode). Alternatively, the light source may supply broadband light that is in turn filtered to select light at a desired wavelength or wavelengths for transmission to the light guide. Thus, in the present device, one or more filters may be transposed between the light source and the light guide. For example, where the light source is a broadband lamp, the device may be equipped with a filter mechanism that selects a single wavelength at a time, or a set of desired wavelengths at a time, from the broadband light prior to transmission of the light to the light guide, and the filtered light (i.e., the selected wavelength or wavelength) is translated to the light guide. A filter may correspond to the excitation wavelength of a molecule found at the target. For example, the device may include a filter corresponding to the excitation wavelength of nicotinamide adenine dinucleotide (NADH), a filter corresponding to the excitation wavelength of flavoprotein (FP), or filters of both varieties. The excitation wavelength of NADH is 360 nm, and the excitation wavelength of FP is 440 nm. In preferred embodiments, the light source and filter mechanism are positioned at or near the distal end of the catheter, and the filtered light translates along the length of the catheter via the lumen to the light guide. For example, the light source may comprise a single broadband lamp, and multiple, selectable filters are used to select a desired wavelength or wavelengths from the light source prior to the delivery of such light to the catheter via the lumen; in such embodiments, the light that enters the catheter and is delivered to the light guide is light of a desired wavelength or wavelengths. In other embodiments, the light source is positioned at or near the distal end of the catheter, and one or more filters are housed within the catheter and are used to select a desired wavelength of light from the light source for delivery to the light guide. One skilled in the art will readily appreciate that the arrangement of the components is incidental to the purpose of delivering light at a desired wavelength or wavelengths to the light guide, and accordingly any arrangement may be selected pursuant to the present invention.

In accordance with the instant invention, light from the light source is translated along some length of the catheter to the light guide. The light guide is located at the proximal end of the catheter and is in optical communication with the lumen, which is adapted for transmitting light from the light source to the light guide. The light guide may be any component that functions as an optical waveguide with respect to the light that is transmitted from the light source via the lumen of the catheter. Planar, strip, slab, rectangular, and fiber waveguides are exemplary light guides, the characteristics of which may be readily appreciated by those skilled in the art. In a preferred embodiment, the light guide is of the optical fiber variety. The light guide permits the transmission of light from the catheter onto a prescribed target region and at a desired intensity. For example, the target region onto which incident light from the light guide is transmitted can be 0.1 mm to 10 mm in diameter, preferably 1 mm to 5 mm in diameter. The light intensity that is incident on the target region at the tip of the light guide may be 0.1 µW to 10 µW, preferably 1 µW to 5 µW.

There may also be filters for selecting one or more wavelengths of light from the light that is received by the light guide from the target, i.e., following irradiation of the target with light from the light guide. When the target is irradiated with light from the light guide, it may emit a fluorescence signal that is transmitted back to the light guide. Filters may be used to obtain one or more desired wavelengths from the fluorescence signal. A filter for this purpose may correspond to the fluorescence emission wavelength of a molecule found at the target. For example, the device may include a filter corresponding to the emission wavelength of nicotinamide adenine dinucleotide (NADH), a filter corresponding to the emission wavelength of flavoprotein (FP), or filters of both varieties. The emission wavelength of NADH is 450 nm, and the emission wavelength of FP is 520 nm.

The instant devices also comprise a detector, which may itself comprise one or more components and/or be capable of performing one or more functionalities. For example, the detector may comprise a photomultiplier for enhancing the signal received from the target via the light guide and catheter. The detector may further comprise a converter for converting the signal to an electric voltage, a digitizer, a display, data acquisition software, or any combination of such features. Any of the components or feature traditionally associated with fluorometry may be included in the instant device. The detector receives the light, e.g., the fluorescence signal, from the light guide via the catheter. Therefore, in addition to functioning to transmit light from the catheter onto a prescribed target region and at a desired intensity, the light guide functions to receive light that is emitted from the target (e.g., a fluorescence signal). Because the light guide is in optical communication with the lumen, the light that is received by the light guide may be translated back along all or part (depending on the location of the emission filter, detector, or both) of the length of the catheter and received by the detector. The detector correlates the fluorescence signal to the mitochondrial function of the cells at the target. As disclosed above, the ratio of the fluorescence signals corresponding to nicotinamide adenine dinucleotide (NADH) and flavoprotein (FP), respectively, may be expressed according to the equation FP/FP+NADH, which is defined as the redox ratio (RR), and has been shown to correlate with different metabolic states and mitochondrial function, including mitochondrial dysfunction associated with apoptosis. Accordingly, the instant devices may be used to assess, inter alia, mitochondrial function and apoptotic potential in a living subject.

The target or site of interest, i.e., the area within a living subject that is studied using the present device, may be any location that is accessible through the vasculature. Alternatively, the target or site of interest may be a location within a body cavity that is accessible through a body orifice, such as the oral cavity. The catheter may be delivered to the target or site of interest through the vasculature, and the initial introduction of the catheter may be achieved via percutaneous delivery. Alternate methods for deploying a catheter to an internal site and positioning a catheter proximate to a site of interest within a subject, are well known among those skilled in the art, and the present disclosure should not be construed as limiting with respect to the method for inserting, guiding, or positioning the catheter within the subject. The target or site of interest may be on, inside, or near ischemic cardiac tissue, dysfunctional cardiac tissue, ischemic brain tissue, an atherosclerotic obstruction of a blood vessel, or a transplanted tissue or organ. Surprisingly, it has presently been discovered that useful readings may be obtained by analysis of a small area of tissue. For example, as disclosed in Example 1, infra, a light guide having a 3 mm diameter tip was used to obtain fluorescence readings from a roughly coextensive portion of ischemic cardiac tissue and accurately assess myocardial infarct size within the ischemic cardiac tissue. The assessment of myocardial injury may be acquired, for example, before myocardial reperfusion, during reperfusion, and/or after reperfusion. The present device may also be used to assess ischemic brain injury by delivering the catheter transvascularly, e.g., via the jugular, to a site within a patient's skull. Such process would be extremely useful for monitoring a patient's brain during a medical procedure where oxygenation of the brain might be compromised, for example, during cardiac surgery.

Monitoring cardiac tissue, brain tissue, an atherosclerotic obstruction, transplanted tissue or organ, or another locus for a site of interest may require the repetition of the process of placing the catheter proximate to the site of interest, acquiring light signals (such as fluorescence signals) from cells at the site of interest (which may be referred to as a detection step), correlating the signals to the mitochondrial function of the cells (which may be referred to as an analytical step), or any combination of these steps. For example, the catheter may be left in place following a first set of detection and analytical steps, and subsequently used to perform one or more additional detection and/or analytical steps. Alternatively, the catheter may be removed from the subject or repositioned within the subject following a first set or sets of detection and analytical steps, and subsequently reintroduced (where appropriate) or repositioned, and subsequently used to perform one or more additional detection and/or analytical steps. For simplicity, the step of "placing a catheter proximate to a site of interest within the subject" can refer to the initial act of introducing a catheter within a subject and positioning the catheter proximate to a site of interest, or an act of moving a catheter within a subject from a first location to a second location so that it is repositioned proximate to a second site of interest that is different from the first location. Thus, all or part of the inventive method may be repeated one or more successive times as desired. Such repetition of all or part of the inventive method may occur at regular or irregular intervals, for example, once per week, once per month, once every two months, once every three months, once every six months, once per year, or at any other regular or irregular interval.

The assessment of mitochondrial function within the cells located at the site of interest can provide useful information pertaining to the necrotic potential, the apoptotic potential, the risk of atherosclerotic rupture, metabolic factors, and other characteristics of the cells at or near the site of interest. Such characteristics, whether indicative of high risk, moderate risk, or low risk of a pathological condition or other condition that may merit therapeutic intervention, may be used, where appropriate, to select a suitable therapy regimen. For example, the present methods and devices may be used to assess mitochondrial function on, inside, or near an atherosclerotic obstruction of a blood vessel, which may in turn be correlated to the stability of the obstruction and the risk of rupture and the initiation of a sudden coronary event. If a risk of rupture in an otherwise minimally occlusive atherosclerotic obstruction is determined to be sufficiently high, then appropriate intervention could be undertaken with respect to such a heretofore "inoffensive" obstruction. Those skilled in the art will readily appreciate the range of appropriate therapies that may be undertaken with respect to an atherosclerotic plaque, such as administration of pharmaceuticals or surgical intervention (e.g., angioplasty, endarterectomy, thrombolytic therapy, or bypass surgery). Likewise, the present methods and devices may be used to assess the stability of a heart transplant. A determination that a transplanted tissue or organ exhibits a high apoptotic potential would indicate ongoing organ rejection and would allow a practitioner to undertake procedures to stabilize the transplanted organ by altering immunosuppressive therapy to treat organ rejection. As provided above, the present methods and devices may also be used to assess the degree of myocardial injury in cardiac tissue prior to, during, and/or following reperfusion. This assessment, which provides a measure of infarct size, can be used to predict the ultimate degree of ventricular remodeling and identify which patients would benefit from early prophylactic therapy to prevent the heart failure associated with uncontrolled post infarction remodeling. Appropriate therapeutic modalities for controlling ventricular remodeling include restraint devices, medication (e.g., angiotensin-converting enzyme (ACE) inhibitors), or injection of stiffening components directly into ventricular tissue.

As used herein, the act of selecting a therapy regimen can comprise one or more of initiation of a new therapy regimen, modulation of an ongoing therapy regimen, or cessation of a previous therapy regimen. A therapy regimen can itself comprise undertaking a course of action whereby one or more of the steps of the instant methods are repeated one or more successive times; for example, a therapy regimen can comprise repeating one or more steps of the method for assessing mitochondrial function at regular or irregular intervals. Thus, a therapy regimen can comprise monitoring a subject by undertaking one or more additional episodes of assessing mitochondrial function.

FIG. 1 provides a stylized depiction of an exemplary device in accordance with the present invention. Shown is catheter 10 comprising a sheath 12 defining a lumen 14. The proximal end of the catheter includes a light guide 16, which, in use, is positioned on, inside, or near a target 17 within the living subject. Light that originates from a light source 18, such as a lamp, is filtered to select a desired wavelength using filters 1 or 2, which may independently correspond to a fluorescence excitation wavelength of a compound. The filtered light is translated along the catheter 10 via the lumen 14 to the light guide 16, which transmits the light onto the site of interest or target 17. The light that is incident on the site of interest or target 17 induces the emission of fluorescence signal ("emitted light") from one or more compounds located at the site of interest or target, e.g., from NADH, FP, or both. At least a portion of the emitted light is transmitted to the light guide 16 and translated along the catheter 10 via the lumen 14. The emitted light reaches a second set of one or more filters 3 or 4, which may independently correspond to a fluorescence emission wavelength of a compound. Each of the filters 1, 2, 3, 4 may be housed within a filter mechanism 20 that may comprise a filter wheel or any other suitable component. An encoder 24 may control the filter mechanism 20 in order to select a desired filter, e.g., to select a desired exitation wavelength prior to irradiation of the site of interest or target 17, or to select a desired emission wavelength following receipt of emitted light from the light guide 16, or both. Once the emitted light has passed through a filter 3 or 4, it may be detected by a photomultiplier tube 22, converted to an electric voltage and digitized by an interface 26, and the resulting signal may be displayed onto a suitable display component 28. In preferred embodiments the displayed signal readings can be used to calculate the redox ratio. Multiple sets of readings may be obtained as desired, for example, over a given period of time or in conjunction with a therapy regimen, such as reperfusion (i.e., at different stages of the reperfusion process, such as before, during, and/or after reperfusion).

Any combination of these and the other disclosed features and steps are contemplated as being within the scope of the instant invention. It should be noted that the invention is not limited in its form, application, or use to the configurations, arrangements of parts, and steps illustrated in the accompanying drawings and description. The terms and phrases used herein to describe the illustrative embodiments of the instant invention and are for clarification purposes only; they are not intended for the purpose of limiting the scope of the present invention. The present invention is further defined in the following example. It should be understood that this example, while indicating embodiments of the invention, is given by way of illustration only, and should not be construed as limiting the appended claims. From the above discussion and the example, one skilled in the art can ascertain the essential characteristics of this invention, and without departing from the spirit and scope thereof, can make various changes and modifications of the invention to adapt it to various usages and conditions.

Example 1

Quantification of Acute Myocardial Injury

A well-characterized rabbit model of ischemia-reperfusion injury was used. See Leshnower B G, et al., *Role of acetaminophen in acute myocardial infarction, Am J Physiol Heart Circ Physiol*, vol. 81, no. 4, pp 2424-2431, June 2006. In order to induce a wider range of mitochondrial disruption and myocardial injury half the animals were treated prior to ischemia with Cyclosporin A (CsA). In this rabbit model, CsA has been shown to inhibit mitochondrial permeability transition pore opening at reperfusion following myocardial ischemia resulting in significantly less necrotic and apoptotic myocyte death. Argaud L, et al., *Specific inhibition of the mitochondrial permeability transition prevents lethal reperfusion injury, J Mol Cell Cardiol*, vol. 38, no. 2, pp 367-374, February 2005. The combination of within group (small differences in ischemic zone size due to varying coronary anatomy) and between group (CsA protection) provided a desirable spectrum of myocardial insult with which to correlate redox ration (RR) measurements.

Surgical Protocol. Animals were treated under experimental protocols approved by the University of Pennsylvania's Institutional Animal Care and Use Committee (IACUC) and in compliance with National Institutes of Health Publication No. 85-23, revised 1996. Thirteen New Zealand white rabbits (3.2-4.0 kg) were studies in two experimental groups: 1) Untreated (UnT) (n=7): 1-hour continuous 20 mL infusion of saline given intravenously prior to ischemia; and, 2) Cyclosporine A (CsA) treatment (n=6): 1-hour continuous 20 mL infusion of a solution of saline and CsA (25 mg/kg) given intravenously prior to ischemia Anesthesia was induced with intramuscular ketamine (70-100 mg/kg), Glycopyrrolate (0.01 mg/kg) and Buprenorphine (0.05 mg/kg). After oral endotracheal intubation, animals were mechanically ventilated (Hallowell EMC Model AWS, Pittsfield, Mass.) with air enriched with 0.6 L/min of oxygen.

Anesthesia was maintained with continuous ketamine infusion (20 mg/kg/hr IV). A high fidelity pressure transducer (Millar Instruments Inc. Houston, Tex.) was placed in the left ventricle via carotid artery for continuous LV pressure measurement. Peripheral arterial blood pressure, heart rate and surface electrocardiogram (ECG) were also continuously monitored (Hewlett Packard 78534C, Palo Alto, Calif.) and recorded (Sonometrics Inc., London, Ontario, Canada). Left atrial blood temperature was measured with an electrical thermometer (Thermalert TH-8 Physiotemp Instrument, Clifton, N.J.) and was maintained between 39-40° C. (normal rabbit body temperature) with a high-efficiency water blanket (Medi-Therm III, Gaymar Industries Inc., Orchard Park, N.Y.).

Next, all animals received a 1-hour, continuous 20 mL infusion of either a phosphate buffered saline (PBS) vehicle (UnT), 25 mg/kg of CsA. A left thoracotomy was performed in the fourth intercostal space and the heart was exposed. A pledgetted suture (3-0 Ti-cron, U.S. Surgical, Norwalk, Conn., USA) was passed around a large branch of the circumflex coronary artery at a distance 50% from the base of the heart toward the apex. Myocardial ischemia was achieved by tightening the coronary artery snare and confirmed by ST elevations on ECG and by the distinct color change of the myocardium. After 30 minutes of ischemia, the coronary artery snare was released and the myocardium was reperfused for 180 minutes.

To provide a specimen of normal myocardium one rabbit under went the same protocol as the UnT group with the exception that no coronary was ligated and no ischemia induced.

Myocardial Fluorescence Spectroscopy. Fluorescence spectroscopy of rabbit myocardium in vivo was conducted with a novel fluorometer (FIG. 1). This fluorometer is a mobile optical-electrical apparatus that collects fluorescence signals of any type of tissue through a 3-mm-tip light guide. The incident light is a broadband mercury arc lamp that can be filtered at four different wavelengths by an air turbine filter wheel rotating at 50 Hz. Consequently, up to four signals could be multiplexed to a photodetector in order to make four-wavelength channel optical measurements of tissue metabolism (FIG. 1). In this experiment two channels were used for excitation and the other two for emission signals. The light intensity that is incident on tissue at the fiber tip is 3 μW. In cardiac fluorometry experiments, the excitation wavelengths of FP and NADH were obtained by filtering the mercury arc lamp at 436 nm and 366 nm resonance lines, respectively, by interference filters 440DF20 and 365HT25 (Omega Optical, Brattleboro, Vt.). The fluorescence intensities are then detected by a photomultiplier tube (PMT model R928, Hamamatsu, Japan), converted to an electric voltage, digitized and displayed.

The fluorometer probe was placed on the epicardial surface in the center of the anticipated region of ischemia and continuous recording of the fluorescence signals for FP and NADH signals was performed during baseline (60 min infusion of saline or CsA), ischemia (30 minutes), and reperfusion (180 minutes). The redox ratio was calculated as FP/(FP+NADH) every five minutes from the continuously recorded FP and NADH. All the redox ratio data points were then normalized by the value at time point t=0. These normalized redox ratio (RR) in each group (UnT=7 and CsA=6) were averaged and expressed as mean±standard deviation at five-minute time points for statistical analysis and ten-minute intervals for spectroscopic graphs.

Analysis of Area at Risk and Infarct Size. At the end of the protocol the coronary snare was reapplied, vascular clamps were used to occlude the aorta, pulmonary artery and inferior vena cava, and the right atrium were incised. Five milliliters of Evans blue dye (1%) (Sigma, St. Louis, Mo.) was injected via the left atrium to delineate the ischemic myocardial risk area (AR). The heart was arrested with intra-atrial bolus of 20 mEq of potassium chloride and the heart was explanted. The left ventricle was sectioned perpendicular to its long axis into 6-7 slices. The thickness of each slice was measured with a digital micrometer and a standardized digital photograph was taken (Casio EX-Z850, Tokyo, Japan). Infarct area (I/AR) was delineated by photographing and measuring the slices after 20 minutes of incubation in 2% triphenyltetrazolium chloride (TTC) at 37° C. All photographs were imported into an image analysis program (Image Pro Plus, Media Cybernetics, Silver Spring, Md., USA) and computerized planimetry was performed. The AR is expressed as a percentage of the LV, and the infarct size is expressed as a percentage of the AR (I/AR).

Transmission Electron Microscopy. To confirm the effect of CsA on mitochondrial integrity, punch biopsies from tissue at the location that had been directly under the fluorometric probe were taken from two animals in the UnT group, two animals in the CsA group and the one normal animal at the conclusion of the reperfusion protocol. Each of these biopsies was preserved in electron microscopy fixative (2.5% glutaraldehyde, 2.0% paraformaldehyde, 0.1M sodium cacodylate) for 24 hours at 4° C. After several washes in 0.1M NaCaC, samples were post-fixed with buffered 2% Osmium tetroxide for 1 hour at 4° C. Subsequent washes in 0.1M NaCaC, H2O, and 2% Aqueous Uranyl Acetate were then used to destain samples. Tissue samples were dehydrated in serial washes of EtOH and Propylene Oxide, prior to a slow infiltration with EPON 812. Finally, samples were cured at 70° C. for 48 hours.

Cured samples were submitted to the Biomedical Imaging Core Facility at the University of Pennsylvania, where they were cut, stained, and imaged on a Jeol-10-10 transmission electron microscope (Jeol Ltd, Akishima, Japan). Random images were captured from each sample for comparative analysis. To assess the degree of mitochondrial disruption, five random images of mitochondria at 30,000× were captured from two control, two CsA-treated, and one normal rabbit. The number of disrupted mitochondria was tallied, along with the total number of mitochondria. The percent disrupted mitochondrion (PDM) was then determined, averaged for each group, and reported.

Statistical Analysis. Group results for the RR, I/AR and PDM are expressed as the mean±standard deviation. The RR was calculated at five-minute intervals during the entire experiment for all animals. To assess between group differences in the RR during pre-ischemia, ischemia and post-ischemia analysis of variance (ANOVA) was used. Where ANOVA revealed significant differences Student's T-test was used to compare the groups at individual time points. Postmortem values for I/AR and PDM were compared using Student's T-test.

At each time point the RR was correlated with both the I/AR using Pearson's correlation test. A p-value<0.05 was considered statistically significant. The software package used for the statistical analysis was SPSS version 11.0 for Windows (SPSS Inc., Chicago Ill.).

Figure 2:
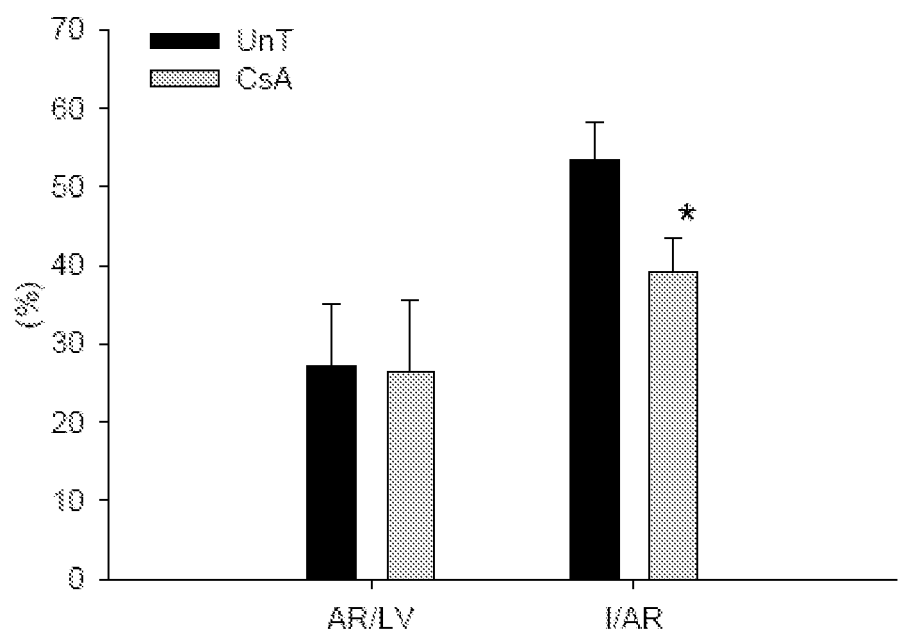
FIG. 2 depicts the results of measurements of ischemic myocardial risk area (AR) as a percentage of the left ventricle (LV), as well as infarct size (I) expressed as a percentage of the ischemic myocardial risk area (AR) in ischemic heart tissue that was either infused with Cyclosporine A in saline (CsA) or saline alone (UnT) prior to ischemia. A statistically significant difference (p<0.01) in the CsA group as compared with the UnT group is indicated by an asterisk.

Results. With respect to infarct size measurements, the two-group model produced a varying degree of infarcted myocardium. FIG. 2 provides a comparison of area at risk and infarct sizes between the UnT group and the CsA group. Values are means standard deviation. The ischemic myocardial risk area (AR) is expressed as a percentage of the left ventricle (AR/LV), and the infarct size is expressed as a percentage of the AR (I/AR). A statistically significant difference from UnT group (p<0.01) is indicated by an asterisk (*). The AR was similar in both groups: 27.0±8.1% in the UnT group and 26.5±9.1% in the CsA group. The I/AR was significantly smaller in the CsA group than in the UnT (39.1±4.4% vs. 53.4±4.7%, p<0.0001) (FIG. 2).

Figure 3:
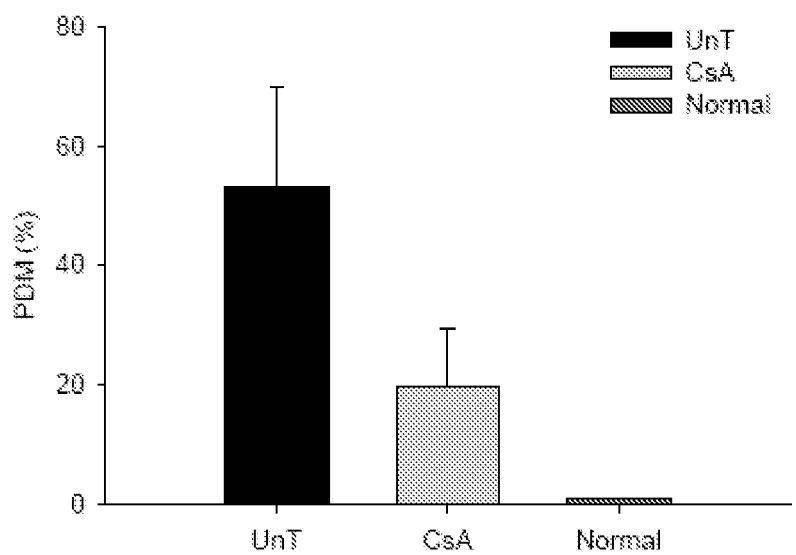
FIG. 3 shows the results of measurements of percent disrupted mitochondria in reperfused ischemic heart tissue that was either infused with Cyclosporine A in saline (CsA) or saline alone (UnT) prior to ischemia, and in normal (non-ischemic) heart tissue.

As for measurements of the extent of mitochondrial disruption, the protective effect of CsA on reperfused myocardium was also quite evident in the myocardial samples studied with EM. The majority of the myocytes in all three groups (one normal, two UnT and two CsA treated rabbits) had nuclei with a ruffled membrane and normally distributed heterochromatin. The nuclear membranes of the normal and the CsA groups were also smooth, while several abnormally shaped nuclei were found in the UnT group. Normally, the nuclear cap, or region surrounding the nucleus, is tightly packed with mitochondria. Although not as densely packed with mitochondria as the normal group, tightly packed mitochondria were still present in the nuclear caps of the CsA group. Most mitochondria of the CsA-treated animals had well-defined outer membranes. Although a small percentage of the mitochondria had dilated cristae, the majority of the CsA cristae exhibited normal characteristics. The nuclear caps of the UnT group were either absent of mitochondria or possessed mitochondria with disrupted outer membranes and tightly packed cristae, vacuolated mitochondria with poorly defined outer membranes, or mitochondria absent of an outer membrane and unraveling cristae. For all three groups, the mitochondria between the muscle fibers possessed characteristics similar to what was found in the nuclear cap of the respective group. FIG. 3 provides a comparison of the percent disrupted mitochondria (PDM) between the UnT group, the CsA group and normal group. Values are means±standard deviation; PDM=percent disrupted mitochondria. The percent disrupted mitochondria for the UnT group was 53.31%±16.47%, for the CsA group, 19.71%±9.64%, and for the normal group 1.65%.

Figure 4:
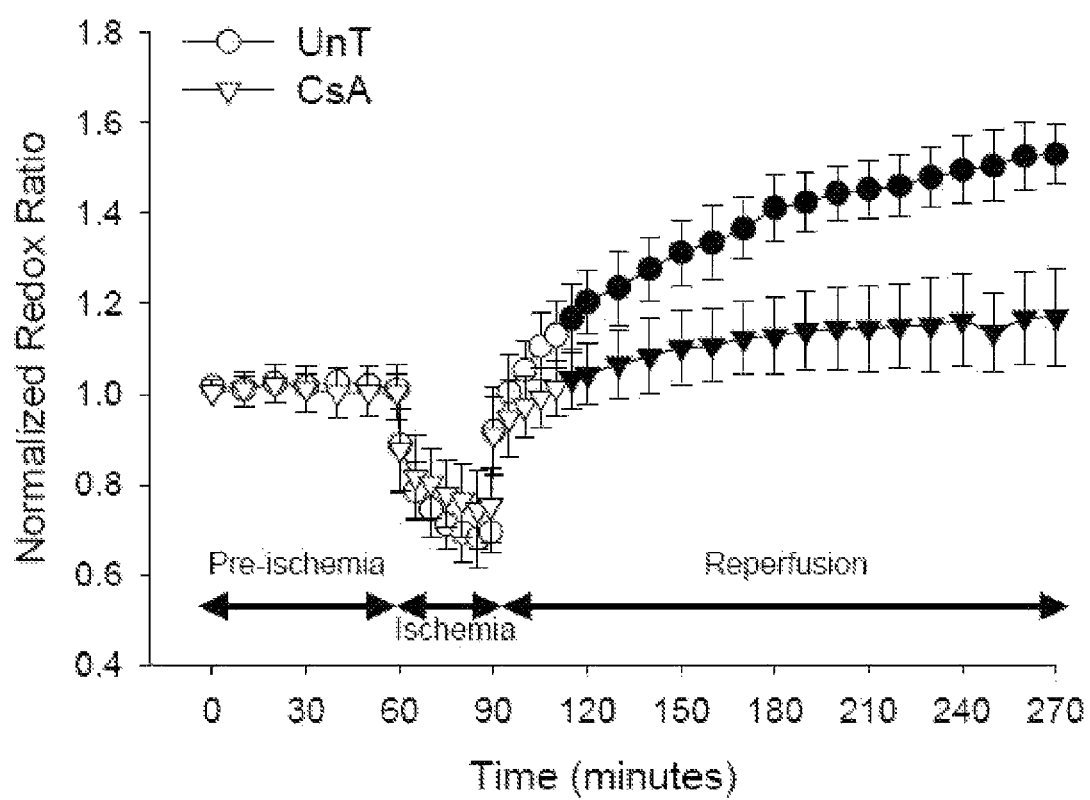
FIG. 4 provides measurements of the normalized redox ratio at ten minute intervals during the periods of pre-ischemia, ischemia, and post-ischemic reperfusion for heart tissue that was either infused with Cyclosporine A in saline (CsA) or saline alone (UnT).

FIG. 4 provides the results of a comparison of mean normalized redox ratio between the UnT group and CsA group at ten-minute intervals throughout the experiment. Statistically significant difference between the UnT and CsA group (p<0.05) is indicated by a filled circle and triangle, respectively. Error bars represent standard deviations from the mean. The RR remained constant in both groups during the pre-ischemic CsA/saline infusion period demonstrating that CsA had no effect on the mitochondrial metabolic state of normally perfused myocardium. In both groups the RR drops immediately with the onset of ischemia and continues to drop steadily during the entire 30 minutes. This is consistent with marked reduction in the oxidative state of the fluorophores due to decrease oxygen availability. That is, NADH and FP remain in their reduced form due to back up of the electron transports chain. The rate at which the RR decreased was slightly less in the CsA group (FIG. 4) but this trend did not reach statistical significance. With the reinstitution of blood flow the RR increased immediately in both groups. In the UnT group the RR increased persistently by 53.1±6.8% over normal during the 180 minutes of reperfusion. This drastic increase in the RR represents a "hyper-oxidation" of fluorophores and is indicative of dysfunctional mitochondria that are unable to reduce $NAD^+$ and FP which prevents their entry into the electron transport chain and ultimately the production of ATP. In the CsA group the RR ratio only increases by 17.0±11.0% of normal demonstrating less mitochondrial dysfunction. During the first 15 minutes after reperfusion the RR increases almost linearly in both groups but with a much greater slope in the UnT group. After 15 minutes of reperfusion the RR of the UnT group is significantly greater than that of the CsA group. After 30 min the RR changes very little in the CsA group.

Table 1, below, demonstrates the correlation between the RR and I/AR at 15 minute time intervals after reperfusion. It can be seen that as early as 15 minutes after reperfusion the RR ratio correlates strongly with infarct size.

TABLE 1

| Minutes of reperfusion | r | p value |
|---|---|---|
| 0 | 0.248 | 0.4132 |
| 15 | 0.695 | 0.0084* |
| 30 | 0.792 | 0.0012* |
| 45 | 0.792 | 0.0012* |
| 60 | 0.807 | 0.0008* |
| 75 | 0.822 | 0.0006* |
| 90 | 0.861 | 0.0002* |
| 105 | 0.863 | 0.0001* |
| 120 | 0.865 | 0.0001* |
| 135 | 0.851 | 0.0002* |
| 150 | 0.838 | 0.0004* |
| 165 | 0.811 | 0.0008* |
| 180 | 0.827 | 0.0005* |

*= statistically significant difference (p < 0.01)

Figure 5:
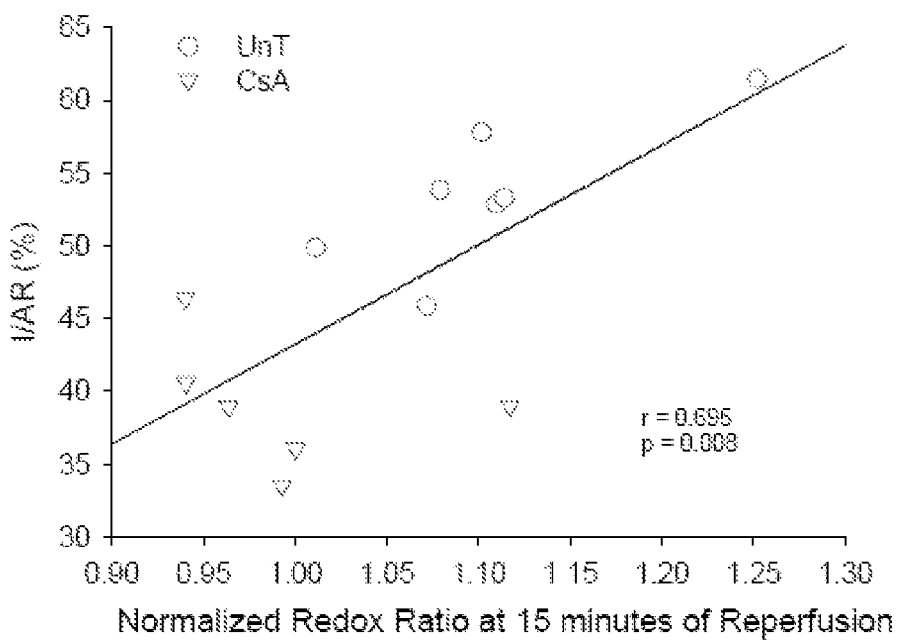
FIGS. 5A and 5B provide scatter plots of the redox ratio (RR) versus the infarct area (I/AR) at 15 minutes and 180 minutes after reperfusion, respectively.
Figure 5:
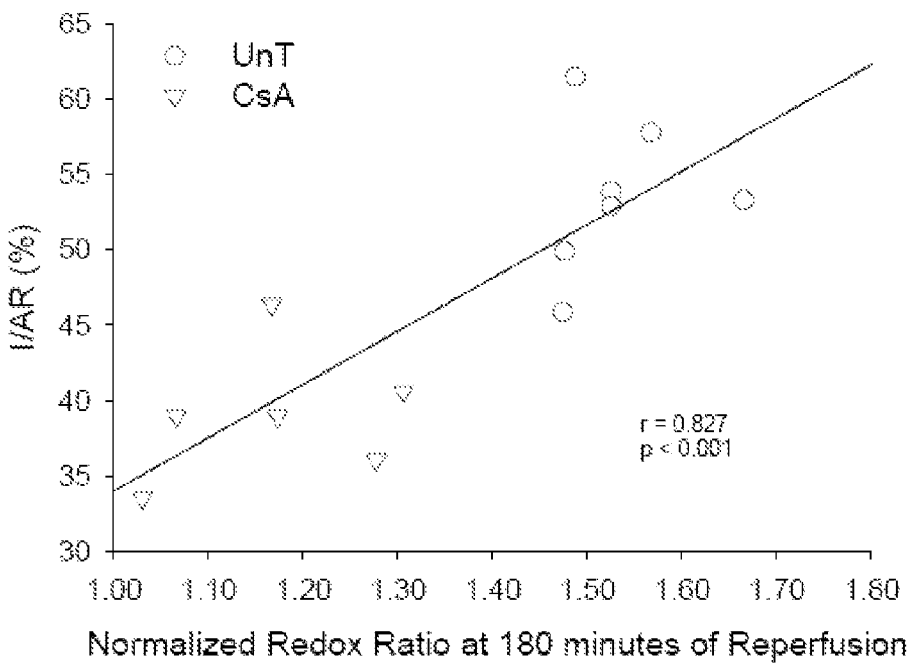

FIGS. 5 and 6 are scatter plots of the RR vs. the I/AR, which demonstrate the predictive strength of the correlation at 15 and 180 minutes after reperfusion, respectively.

Mitochondrial permeability transition (MPT) pore opening is recognized as a pivotal event in necrotic and apoptotic cell death. Kroemer G, et al., *The mitochondrial death/life regulator in apoptosis and necrosis*, Annu Rev Physiol, vol. 60, pp 619-642, 1998; Duchen M R, et al., *On the involvement of a cyclosporin A sensitive mitochondrial pore in myocardial reperfusion injury,*" Cardiovasc Res, vol. 27, no. 10, pp 1790-1794, October 1993. Following myocardial ischemia-reperfusion injury, opening of this nonspecific pore results in inner membrane potential collapse, uncoupling of the respiratory chain, and efflux of small molecules such as cytochrome c and other proapoptotic factors. Zoratti M & Szabo I, *The mitochondrial permeability transition*, BichimBiophys Acta, vol. 1241, no. 2, pp 139-176, July 1995. CsA is a powerful inhibitor of the MPT pore, and several reports indicate that it protects the isolated heart from ischemia-reperfusion injury. Argaud L, et al., *Specific inhibition of the mitochondrial permeability transition prevents lethal reperfusion injury,*" J Mol Cell Cardiol, vol. 38, no. 2, pp 367-374, February 2005. In this study the protective role of CsA was confirmed in vivo and exploited to provide an experimental model with a spectrum of reperfusion induced mitochondrial dysfunction and resulting myocardial injury. This model was used to test the hypothesis that changes in mitochondrial NADH and FP fluorescence can be measured and correlated with myocardial injury.

The preceding data indicates that myocardial reperfusion injury is associated with mitochondrial disruption which is significantly blunted by CsA and that this injury correlates very strongly with the RR as measured by fluorometry. This is particularly compelling considering that the fluorometric measurements of NADH and FP were made over a relatively small epicardial region of the area at risk. We found it equally interesting that even very early after reperfusion (15 minutes) the RR began to correlate with infarct size at 3 hours post reperfusion.

The present studies provide convincing evidence that the instant devices and methods can be used clinically to assess myocardial injury noninvasively without tissue biopsy. Such tools and techniques will provide a better early evaluation of the effectiveness of reperfusion therapy and identify patients that are at increased risk for post infarction ventricular remodeling. Early identification of such patients permits the initiation of more aggressive infarct restraint procedures to prevent heart failure than would be justifiable without proper patient identification.

Furthermore, apoptotic induced mitochondrial dysfunction is associated with established chronic heart failure (Narula J, et al., *Apoptosis in myocytes in end-stage heart failure, N Engl J Med*, vol. 335, no. 16, pp 1182-1189, October 1996) as well as myocardial rejection after heart transplantation (Narula J, et al., *Annexin-V imaging for noninvasive detection of cardiac allograft rejection, Nat Med*, vol. 7, no. 12, pp 1347-1352, December 2001). Both of these conditions are traditionally treated with complex pharmacological strategies, which can be difficult to optimize. The present invention demonstrates that it is possible that fluorometry can be used to assess and monitor the progression of these diseases without tissue biopsy and allow physicians to make more informed decisions regarding drug selection and dosing. Furthermore, the instant catheter-based fluorometer, which can be introduced via standard percutaneous venous or arterial techniques, can be used to assess the myocardial injury associated with reperfusion, ventricular remodeling, and allograft rejection. It can also be used to assess the mitochondrial dysfunction within coronary plaques. Such a measurement could be used as a predictor of the potential for plaque rupture and the associated acute coronary artery occlusion. Such a technology represents a novel route for improving the care of very complex patient conditions while at the same time minimizing patient discomfort and treatment risk.

Additional information regarding the present invention may be found in Mahsa Ranji, Muneaki Matsubara, Bradley G. Leshnower, Robin Hinmon, Dwight L. Jaggard, and Britton Chance, Robert C. Gorman, Joseph H. Gorman III, "*Quantifying acute myocardial injury using ratiometric fluorometry,*" submitted to *IEEE Transaction on Biomedical Engineering* (*TBME*), which is incorporated herein by reference in its entirety.

What is claimed:

1. A method for assessing mitochondrial function in a living subject comprising:
   placing a catheter proximate to a site of interest within said subject;
   using said catheter to acquire fluorescence signals from cells at said site of interest, wherein said signals correspond to fluorescence from mitochondrial nicotinamide adenine dinucleotide and flavoprotein;
   calculating a ratio of fluorescence from mitochondrial nicotinamide adenine dinucleotide to fluorescence from flavoprotein; and,
   correlating said ratio to the mitochondrial function of said cells.

2. The method according to claim 1 wherein said site of interest is located on, inside, or near ischemic cardiac tissue, dysfunctional cardiac tissue, ischemic brain tissue, an atherosclerotic obstruction of a blood vessel, or a transplanted tissue or organ.

3. The method according to claim 1 further comprising correlating said mitochondrial function to the apoptotic potential of said cells.

4. The method according to claim 2 wherein said site of interest is located on, inside, or near ischemic cardiac tissue, and said fluorescence signals are acquired prior to, during, or subsequent to myocardial reperfusion of said subject.

5. The method according to claim 4 further comprising correlating said ratio to myocardial infarct size within said ischemic cardiac tissue.

6. The method according to claim 1 further comprising repeating all or part of said method one or more successive times.

7. The method according to claim 6 wherein said repetition of said method occurs once per week, once per month, once every two months, once every three months, once every six months, or once per year.

8. The method according to claim 1, further comprising, based on an assessment of the mitochondrial function of said cells, selecting a therapy regimen for said subject.

9. A device for assessing mitochondrial function in a living subject comprising:
   a catheter comprising a sheath defining a lumen, a distal end, and a proximal end comprising a light guide for radiating light onto a target within said subject and for receiving a fluorescence signal from said target;
   a light source, wherein said catheter is adapted for transmitting light from said light source to said light guide;
   a 360 nm filter and a 440 nm filter for selecting corresponding wavelengths of light from said light source prior to transmission to said light guide;
   a 450 nm filter and a 520 nm filter for selecting corresponding wavelengths of light from said fluorescence signal prior to transmission to said detector; and,
   a detector for receiving said fluorescence signal from said light guide, for obtaining a ratio of fluorescence signals corresponding to nicotinamide adenine dinucleotide to fluorescence signals corresponding to flavoprotein, and for correlating said ratio to the mitochondrial function of said target.

10. The device according to claim 9 wherein said light source delivers light to said lumen via said distal end of said catheter.

11. The device according to claim 10 wherein said light source comprises a lamp or a laser.

12. The device according to claim 11 wherein said catheter comprises optical fibers for transmitting light from said light source from said light guide.

13. The device according to claim 9 wherein said light source is housed within said lumen.

14. The device according to claim 9 wherein said light guide comprises an optical fiber.

15. The device according to claim 9 wherein said detector comprises a photomultiplier and a digitizer.

* * * * *

UNITED STATES PATENT AND TRADEMARK OFFICE
CERTIFICATE OF CORRECTION

PATENT NO.        : 8,473,036 B2
APPLICATION NO.   : 12/935755
DATED             : June 25, 2013
INVENTOR(S)       : Gorman, III et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 270 days.

Signed and Sealed this
Eighth Day of September, 2015

Michelle K. Lee
*Director of the United States Patent and Trademark Office*